United States Patent
Roeck et al.

(10) Patent No.: US 11,044,564 B2
(45) Date of Patent: Jun. 22, 2021

(54) HEARING SYSTEMS AND METHODS FOR OPERATING A HEARING SYSTEM

(71) Applicant: SONOVA AG, Staefa (CH)

(72) Inventors: Hans-Ueli Roeck, Hombrechtikon (CH); Christian Frei, Staefa (CH); Konstantin Silberzahn, Meilen (CH); Markus Mueller, Männedorf (CH); Markus Leuthold, Stäfa (CH)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 16/587,896

(22) Filed: Sep. 30, 2019

(65) Prior Publication Data

US 2021/0099811 A1    Apr. 1, 2021

(51) Int. Cl.
*H04R 25/00*      (2006.01)
*A61B 5/00*       (2006.01)
(Continued)

(52) U.S. Cl.
CPC ......... *H04R 25/505* (2013.01); *A61B 5/6817* (2013.01); *G10K 11/17823* (2018.01); *H04R 25/405* (2013.01); *H04R 25/407* (2013.01); *H04R 25/554* (2013.01); *H04R 25/604* (2013.01); *H04R 25/609* (2019.05); *H04R 25/652* (2013.01); *A61B 5/01* (2013.01); *A61B 5/021* (2013.01); *A61B 5/02416* (2013.01); *A61B 5/14532* (2013.01); *A61B 5/318* (2021.01); *A61B 5/369* (2021.01);
(Continued)

(58) Field of Classification Search
CPC .... H04R 25/405; H04R 25/45; H04R 25/453; H04R 25/556; H04R 25/607; H04R 2225/0213; H04R 2225/0216; H04R 2460/01; H04R 2460/05; H04R 2460/11
See application file for complete search history.

(56) References Cited

U.S. PATENT DOCUMENTS 8,798,294 B2 *   8/2014   Havenith ............. H04R 25/505
                                                         381/314
9,693,154 B2 *   6/2017   Higgins ............... H04R 25/556
                          (Continued)

FOREIGN PATENT DOCUMENTS

DE    102005006404          8/2006
WO    WO-2010034337 A1 *    4/2010   ............ H04R 25/60
WO    WO-2018117997 A1 *    6/2018   ............ H04R 25/652

*Primary Examiner* — Ryan Robinson
(74) *Attorney, Agent, or Firm* — ALG Intellectual Property, LLC (57) ABSTRACT

An exemplary hearing system that is configured to assist a user in hearing includes a behind-the-ear (BTE) component that includes a power source and an in-the-ear (ITE) component configured to fit at least partially within an ear canal of the user. The ITE component may include a microphone arranged so as to face outside of the ear canal of the user while the ITE component is worn by the user, a vent opening configured to ventilate the ear canal of the user to an environment outside of the ear canal, a receiver configured to provide an audio signal to the user based on an input audio signal detected by the microphone, and at least one of active noise control circuitry configured to reduce at least one of environmental noise entering the ear canal through the vent opening and occlusion and an active vent configured to control the vent opening.

19 Claims, 5 Drawing Sheets

(51) Int. Cl.
*G10K 11/178* (2006.01)
*A61B 5/01* (2006.01)
*A61B 5/021* (2006.01)
*A61B 5/024* (2006.01)
*A61B 5/145* (2006.01)
*A61B 5/318* (2021.01)
*A61B 5/369* (2021.01)
*A61B 5/398* (2021.01)

(52) U.S. Cl.
CPC ......... *A61B 5/398* (2021.01); *A61B 2562/029* (2013.01); *A61B 2562/06* (2013.01); *G10K 2210/1081* (2013.01); *H04R 2225/021* (2013.01); *H04R 2225/025* (2013.01); *H04R 2460/11* (2013.01)

(56) References Cited

U.S. PATENT DOCUMENTS

| | | | | |
|---|---|---|---|---|
| 2008/0247561 | A1* | 10/2008 | Smith | H04R 1/1075 381/72 |
| 2009/0262964 | A1 | 10/2009 | Havenith | |
| 2015/0078600 | A1* | 3/2015 | Rasmussen | H04R 25/453 381/318 |
| 2019/0132683 | A1* | 5/2019 | Sacha | A61B 5/0476 |
| 2019/0394576 | A1* | 12/2019 | Petersen | H04R 25/453 |
| 2020/0288253 | A1* | 9/2020 | De Haan | H04R 25/556 |

* cited by examiner

HEARING SYSTEMS AND METHODS FOR OPERATING A HEARING SYSTEM

BACKGROUND INFORMATION

Hearing systems are used to improve the hearing capability and/or communication capability of users. Such hearing systems are configured to process a received input sound signal (e.g., ambient sound) and then provide the processed input sound signal to the user (e.g., through a hearing device such as a hearing aid). Hearing systems come today in three fundamentally different form factors. First, behind-the-ear ("BTE") devices with all electric and electronic components including microphone and transducers behind a pinna, second, in-the-ear ("ITE") devices with all electric and electronic components including microphone and transducers being in a concha and/or an ear canal, and third, receiver-in-the-canal ("RIC") devices, which have all components except a receiver (also referred to as a speaker) behind the pinna while the receiver is placed in the ear canal as an ITE component.

As hearing systems have evolved, an increasing number of components (e.g., further microphones, a larger receiver, an active vent, physiologic sensors in the ear, etc.) have been added to the ITE components and/or the BTE components to improve their functionality. However, adding even more components to especially the ITE component is difficult due to limited space constraints within the ITE component, leading to a large ITE component filling the entire concha or even sticking out of the ear. Commercial hearing systems such as "Hearables" are typical examples that stick out of the ear and, as a result, have a center of gravity that is out of the ear canal, which leads to their tendency to fall out of the ear.

In addition, adding further components to an ITE component in a RIC configuration may require adding additional wiring between the ITE component and the BTE component to facilitate communication between the additional components and the BTE component. Such additional wiring may undesirably increase the size of a cable connecting the BTE component to the ITE component and/or generate interference.

Moreover, in conventional hearing systems, the configuration of certain components may result in sub-optimal operation of a hearing system. For example, a microphone positioned on a BTE component may be shielded by a pinna of an ear of a user and/or may have a detection axis that may face either backward or upward. Such a configuration results in the microphone having a poor beamforming capability to the front of the user where target sources may be located. Thus, a microphone may be placed in the concha or canal of an ear to provide better audio pickup properties and a more natural sound. However, the proximity of such a microphone to a vent reduces the available gain before feedback.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Hearing systems and methods for operating a hearing system are described herein. As will be described in more detail below, an exemplary hearing system configured to assist a user in hearing may include a BTE component and an ITE component. The BTE component is configured to fit behind an ear of the user and includes a power source. The ITE component is configured to fit at least partially within an ear canal of the user while the hearing system is worn by the user. The ITE component may include a microphone arranged so as to face outside of the ear canal of the user while the ITE component is worn by the user, a vent opening configured to ventilate the ear canal of the user to an environment outside of the ear canal while the ITE component is worn by the user, and a receiver configured to provide an audio signal to the user based on an input audio signal detected by the microphone. In addition, the ITE component may include at least one of active noise control circuitry configured to reduce at least one of environmental noise entering the ear canal through the vent opening and occlusion and an active vent configured to control the vent opening in the ITE component.

In certain alternative implementations, an exemplary hearing system configured to assist a user in hearing may include a BTE component configured to fit behind an ear of the user, an ITE component configured to fit at least partially within an ear canal of the user while the hearing system is worn by the user, and a cable that communicatively couples the BTE component with the ITE component. The BTE component may include a power source and a wireless communication device. The ITE component may include a microphone arranged so as to face outside the ear canal of the user while the ITE component is worn by the user, a processor configured to process an input audio signal detected by the microphone, and a receiver configured to provide an audio signal to the user based on the input audio signal detected by the microphone and processed by the processor.

By providing hearing systems with BTE components and ITE components configured according to principles described herein, it is possible to improve functionality of BTE components and/or ITE components. For example, by providing an ITE component with one or more microphones configured such as described herein, it is possible to improve a beamformer effect (e.g., with respect to sound from a front of a user). In addition, it is possible to place a vent opening such that feedback is impinging from a direction in the back hemisphere while utilizing active noise canceling methods in combination with relatively small vent sizes to reduce feedback. Further, by utilizing configurations such as those described herein, it is possible to optimize space within ITE components so that they may include additional and/or alternative components (e.g., one or more physiological sensors, a relatively more powerful receiver, etc.) that otherwise would not fit in conventional ITE components. Furthermore, a goal of the present disclosure is to define a configuration of components in the ear canal and behind the ear that allows for beneficial functionalities while keeping the ITE components and BTE components of a hearing system small and cosmetically appealing and concurrently reducing sensitivity to electrical interference due to many wires that may otherwise be provided between the ITE component and the BTE component of the hearing system. Other benefits of the hearing systems and methods such as those described herein will be made apparent herein.

Figure 1:
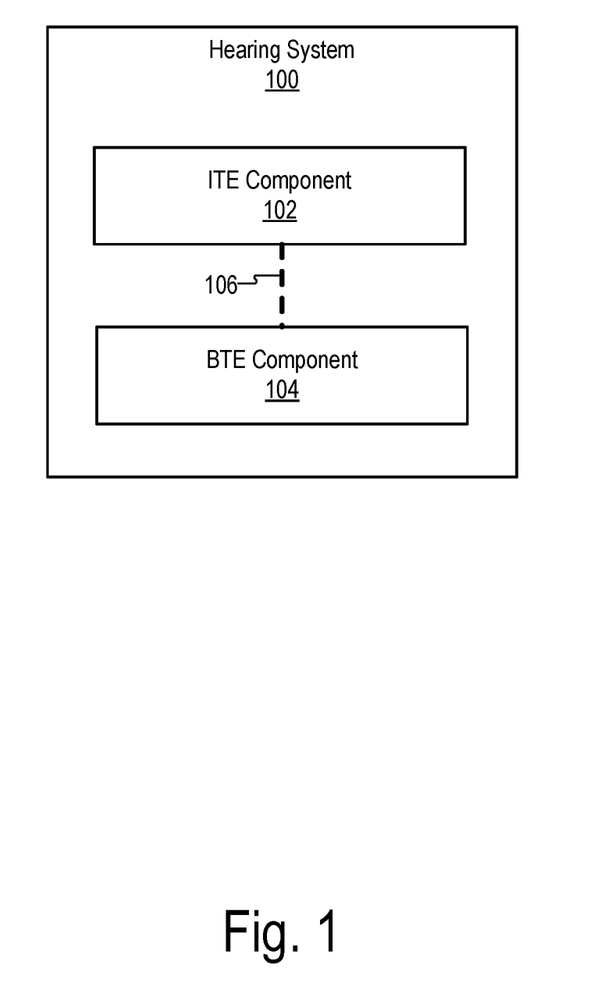
FIG. 1 illustrates an exemplary hearing system according to principles described herein.

FIG. 1 illustrates an exemplary hearing system 100 that is configured to assist a user in hearing. As shown, hearing system 100 may include, without limitation, an ITE component 102 and a BTE component 104 that are communicatively coupled to one another by way of a cable 106.

ITE component 102 is configured to fit at least partially within an ear canal of a user while hearing system 100 is worn by the user. ITE component 102 may have any suitable combination of components as may serve a particular implementation. Any suitable type of ITE component may be used for ITE component 102 as may serve a particular implementation. For example, in certain implementations, ITE component 102 may be configured to be provided completely within the ear canal of a user when worn by the user. In certain alternative examples, at least part of ITE component 102 may extend outside of the ear canal while at least part of the ITE component is provided within the ear canal. For example, in certain implementations, part of ITE component 102 may extend within a concha of the ear of the user. To illustrate, ITE component 102 may include a retention member such as a flexible fin configured to extend within the concha and retain ITE component 102 in the ear canal.

In certain examples, ITE component 102 may be custom made to fit a particular user. For example, ITE component 102 may have a custom formed shell and/or faceplate formed by any suitable process (e.g., a three-dimensional printing process, a custom molding process, etc.). Alternatively, ITE component 102 may be implemented by a one-size-fits-all solution implemented by a dome, a foam, a rubber, or any other suitable type of material/structure that is then deformed to fit a particular user. In such examples, the ITE component may be shaped to fit a particular user through, for example, methods that include using an ultra-violet curable plastic or using shape memory materials that retain their ability to change their shape after being cooled down. Exemplary components that may be included as part of ITE component 102 will be described herein.

BTE component 104 is configured to fit behind an ear of a user while hearing system 100 is worn by the user. BTE component 104 may include any suitable component or combination of components as may serve a particular implementation. For example, BTE component 104 may include a power source (e.g., a battery) that is configured to provide operating power to ITE component 102 by way of cable 106. Exemplary components that may be included as part of BTE component 104 will be described herein.

Cable 106 is configured to communicatively couple BTE component 104 with ITE component 102. Cable 106 may be configured in any suitable manner as may serve a particular implementation. In certain examples, cable 106 may be fixed (e.g., not removable) at each end to ITE component 102 and BTE component 104 respectively. In certain alternative implementations, cable 106 may have a connector portion on one end such that cable 106 is removably attachable to one of BTE component 104 and ITE component 102. Alternatively, cable 106 may have a connector portion on each end of cable 106 such that cable 106 is removably attached to both BTE component 104 and ITE component 102. Such a connector portion may have any suitable configuration as may serve a particular implementation. By configuring cable 106 with one or more connector portions, it is possible to easily replace cable 106, for example, when cable 106 is damaged or when a cable of a different length is desired. In addition, by configuring cable 106 with one or more connector portions, it is possible to easily replace either ITE component 102 or BTE component 104 should either of them become damaged. As such, it is possible to avoid having to replace all of the components in hearing system 100 if only one of them is damaged or otherwise needs to be replaced.

Cable 106 may include any suitable component to facilitate communicatively coupling BTE component 104 to ITE component 102. For example, in certain implementations, cable 106 may include one or more of a wire and an optical fiber to facilitate BTE component 104 communicating with ITE component 102. In examples where cable 106 includes on optical fiber, an optical transceiver may be provided in each of ITE component 102 and BTE component 104. Additionally or alternatively, cable 106 may use a serial bus to facilitate communication between BTE component 104 and ITE component 102. Any suitable type of serial bus may be used as may serve a particular implementation. For example, the serial bus may include one of a proprietary bus, an inter-integrated circuit bus, a serial peripheral interface bus, an improved inter-integrated circuit bus, an optical bus, and an electrical system bus.

Cable 106 may have any suitable length as may serve a particular implementation. In certain examples, cable 106 may have a fixed length. In such examples, a plurality of cables 106 of different lengths may be available for selection based on the anatomical features of the ear of a particular user. Each cable included in the plurality of cables 106 may be removably attached (e.g., through connector portions on each end) to BTE component 104 and ITE component 102 such that the user may easily swap in/out different sized cables 106, as needed, to select a cable 106 that best fits the user.

In certain alternative examples, the length of cable 106 may be repeatably adjustable to facilitate fitting hearing system 100 to a particular user. For example, cable 106 may include a movable tube that has an adjustable length. Such a movable tube may be configured in any suitable manner. For example, a movable tube may include two or more tubes that telescopically extend with respect to one another when a length of cable 106 is increased or decreased. In such examples, the wiring, the optical fiber, etc. provided as part of cable 106 may be coiled such that they may absorb the increase or decrease in length without breaking. With such a configuration, the wire and/or the optical fiber included within cable 106 may be straightened when a distance between BTE component 104 and ITE component 102 increases and coil when the distance between BTE component 104 and ITE component 102 decreases.

Figure 2A:
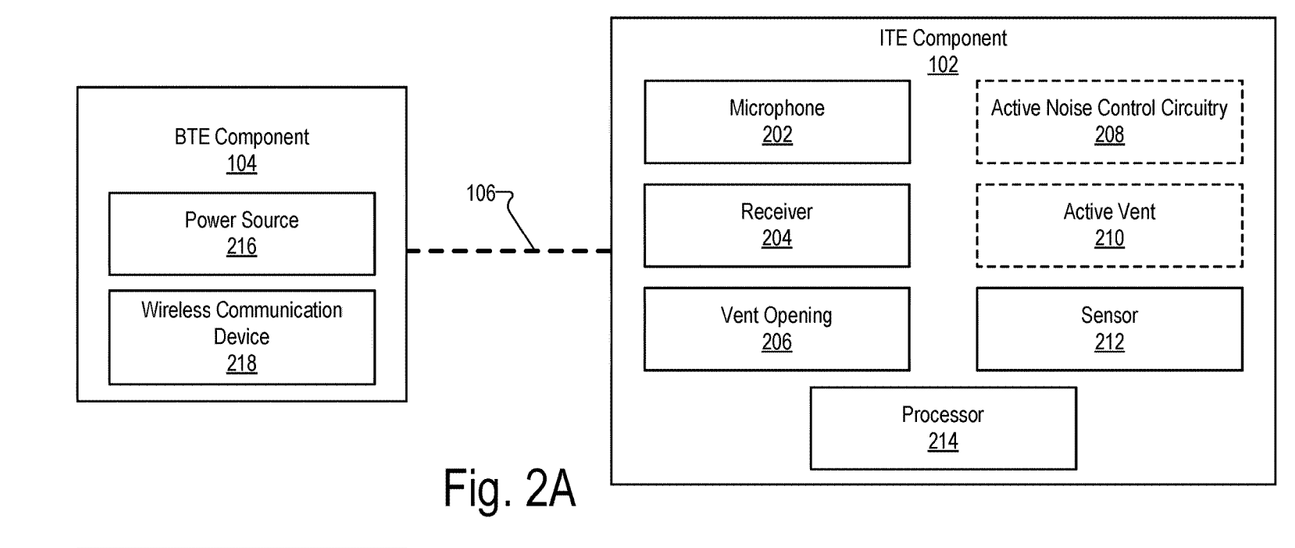
FIGS. 2A and 2B illustrate exemplary components that may be included as part of BTE components and ITE components that may be provided according to principles described herein.
Figure 2B:
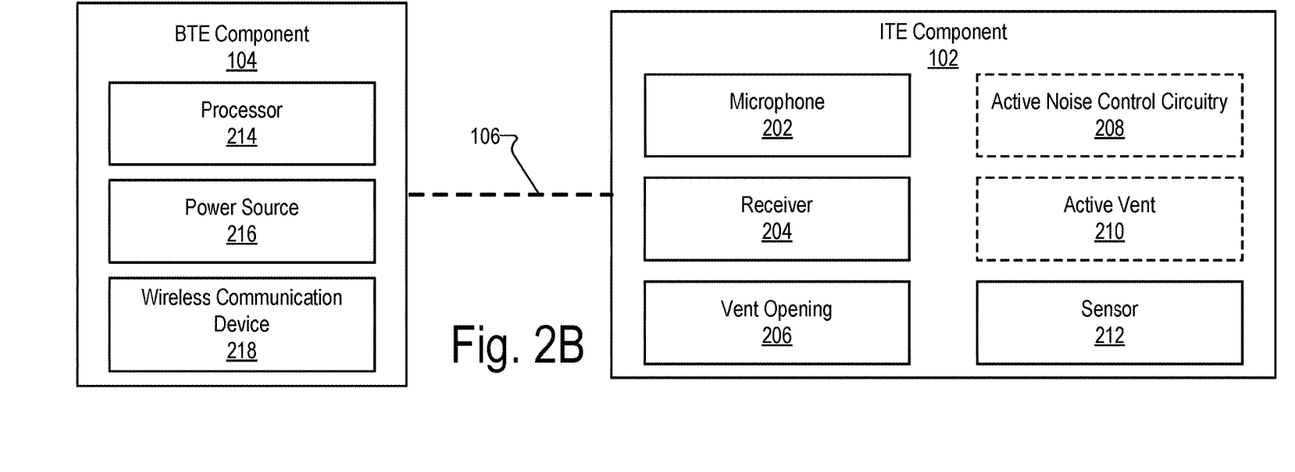

FIGS. 2A and 2B show exemplary components that may be included as part of ITE component 102 and BTE component 104 according to certain implementations. As shown in FIG. 2A, ITE component 102 may include, without limitation, a microphone 202, a receiver 204, a vent opening 206, active noise control circuitry 208, an active vent 210, a sensor 212, and a processor 214. Active noise control circuitry 208 and active vent 210 are shown in dashed lines in FIGS. 2A and 2B because they may be optionally provided as part of ITE component 102. In certain examples, both active noise control circuitry 208 and active vent 210 may be provided as part of ITE component 102. Alternatively, only one or none of noise control circuitry 208 and active vent 210 may be provided as part of ITE component 102. As is further shown in FIG. 2A, BTE component 104 may include, without limitation, a power source 216 and a wireless communication device 218. Each of these components will now be described in detail.

Microphone 202 may be configured to detect audio signals presented to the recipient. Microphone 202 may be implemented in any suitable manner. For example, microphone 202 may include a microphone that is arranged so as to face outside an ear canal of a user while ITE component 102 is worn by the user. In certain examples, microphone 202 may be implemented by a microphone that is configured to be placed within the concha of the ear near the entrance to the ear canal. Such a microphone may be a boom microphone that is held within the concha of the ear near the entrance of the ear canal by a boom or stalk that is attached to ITE component 102. Additionally or alternatively, microphone 202 may be implemented by one or more microphones provided on a faceplate of ITE component 102, an ear canal microphone, one or more beam-forming microphones, and/or any other suitable type of microphone or combination of microphones as may serve a particular implementation. By arranging microphone 202 as part of ITE component 102, it is possible to orient an axis of microphone 202 to the front of the user, use microphone 202 for active noise cancelling, and/or improve a beamforming capability of microphone 202 as compared to conventional hearing systems in which a microphone is provided on a BTE component.

In certain examples, microphone 202 may be implemented as part of a directional microphone configuration in which a first microphone and a second microphone are arranged so as to face outside of the ear canal of the user while ITE component 102 is worn by the user. In such examples, sound coming from in front of the user is favored by the first and second microphones and sound coming from directions other than in front of the user is attenuated by the first and second microphones.

Receiver 204 (also referred to as a speaker) may be implemented by any suitable electroacoustic output transducer configured to acoustically represent an audio signal to a user. Receiver 204 may be included as part of ITE component 102 in any suitable manner. For example, in certain implementations, receiver 204 may be configured so as to be placed in the ear canal of the user to directly deliver sound into the ear canal. Receiver 204 may be implemented by a balanced armature type in certain implementations. In certain alternative implementations, receiver 204 may be implemented by a dynamic (moving coil) speaker type.

Vent opening 206 is configured to ventilate the ear canal of the user to an environment outside of the ear canal while ITE component 102 is worn by the user. Vent opening 206 may be statically configured to allow more or less unamplified sound from the environment outside of the ear canal to pass through ITE component 102 and into the ear canal. In addition, sound from by receiver 204 may pass through vent opening 206 to the environment outside the ear canal in certain examples.

Vent opening 206 may be provided at any suitable position on ITE component 102 as may serve a particular implementation. For example, vent opening 206 may be positioned on ITE component 102 toward a back of the user's head as compared to microphone 202. With such a configuration, vent opening 206 may be positioned such that the sound from receiver 204 that exits vent opening 206 impacts microphone 202 (and/or an additional microphone) from a direction that causes sound from receiver 204 to be attenuated (e.g., by way of a directional microphone configuration).

Active noise control circuitry 208 is configured to reduce remaining environmental noise entering the ear canal through the vent opening and/or reduce occlusion artefacts (e.g., the perception of the user's own voice as being too loud, "boomy," or "hollow"). Active noise control circuitry 208 may be configured to utilize any suitable configuration of components to facilitate reducing environmental noise and/or occlusion. For example, in certain implementations, ITE component 102 may include an ear canal microphone arranged so as to face inside an ear canal of a user while ITE component 102 is worn by the user. In such examples, active noise control circuitry 208 may be configured to use such an ear canal microphone in any suitable manner to reduce the environmental noise and/or occlusion artefacts. Additionally or alternatively, ITE component 102 may include a dynamic speaker configured to be provided within the concha of the ear of the user while ITE component 102 is worn by the user. In such examples, active noise control circuitry 208 may be configured to use such a dynamic speaker in any suitable manner to reduce the environmental noise and/or occlusion artefacts.

An active vent 210 may be configured to dynamically control opening and closing of vent opening 206 in ITE component 102. Active vent 210 may be configured to control vent opening 206 by way of any suitable mechanism and in any suitable manner. For example, active vent 210 may be implemented by an actuator that opens or closes vent opening 206 based on a detection of the user's own voice and/or different acoustical situations. One example of an actuator that may be used as part of active vent 210 is an electroactive polymer that exhibits a change in size or shape when stimulated by an electric field. In such examples, the electroactive polymer may be placed in vent opening 206 or any other suitable location within ITE component 102. In a further example, active vent 210 may use an electromagnetic actuator to open and close vent opening 206. In a further example, active vent 210 may not only fully open and close, but may be positioned in any one of various intermediate positions (e.g., a half open position, a one third open position, a one fourth open position, etc.). In a further example, active vent 210 may be closed while streaming sound from an additional device to hearing system 100 or while playing back such sound from a memory within hearing system 100.

Hearing system 100 may differentiate between the user's own voice, quiet environments, feedback, music, etc. If hearing system 100 detects the user's own voice speaking at a conversational level (e.g., at least 55 decibels sound pressure level), hearing system 100 may cause active vent 210 to open vent opening 206 in any suitable manner. On the other hand, in quiet environments, when significant gain is to be applied to an input audio signal detected by microphone 202, and/or if feedback is identified, hearing system 100 may cause active vent 210 to close vent opening 206.

Sensor 212 may include any suitable sensor or combination of sensors that may be used to detect an aspect associated with a user of hearing system 100. In certain examples, sensor 212 may be implemented by a physiological sensor configured to detect a physiological attribute of a user while hearing system 100 is worn by the user. As used herein, a "physiological attribute" may refer to any characteristic that may be associated with the functioning of the body of the user of hearing system 100. To facilitate detecting a physiological attribute, sensor 212 may include, but is not limited to, one or more of a photoplethysmogram sensor, a humidity sensor, a body temperature sensor, a glucose sensor, a blood pressure sensor, an electrocardiogram ("ECG") sensor, an electrooculography sensor, an electroencephalogram sensor, and/or any other suitable sensor.

In certain examples, sensor 212 may be implemented by one or more sensor electrodes configured facilitate hearing system 100 detecting a physiological attribute of the user while hearing system 100 is worn by the user. Such sensor electrodes may be arranged in any suitable manner to facilitate detection of a physiological attribute.

To illustrate an example, a sensor electrode may be configured to be provided on a surface of ITE component 102 and is configured to contact outer ear tissue of the user while hearing system 100 is worn by the user. As used herein, "outer ear tissue" refers to any tissue of the ear that is either inside the ear canal or that is outside of the ear canal. For example, any portion (e.g., the helix, the concha, etc.) of the pinna of the ear may be considered as outer ear tissue for the purposes of this disclosure. An additional sensor electrode may be configured to be located at an entrance to or outside of the ear canal of the user while hearing system 100 is worn by the user. In certain examples, the additional sensor electrode may be located on a surface of ITE component 106 that is at the entrance to or outside of the ear canal. While the sensor electrode contacts the outer ear tissue, the additional sensor electrode may be configured to contact a finger of the user to facilitate taking, for example, an ECG measurement of the user.

Additionally or alternatively, ITE component 102 may include, without limitation, a compass, a gyroscope, an accelerometer, and/or any other suitable component in certain implementations.

Processor 214 is configured to perform any suitable processing operation that may be associated with hearing system 100. For example, such processing operations may include processing an input audio signal detected by microphone 202 and directing receiver 204 to provide an audio signal to a user. Processor 214 may be implemented by any suitable combination of hardware and/or software components (e.g., processors, memories, communication interfaces (analog and/or digital), instructions stored in memory for execution by the processors, etc.).

In addition, processor 214 is configured to perform any suitable processing operation associated with hearing system 100 controlling active noise control circuitry 208, active vent 210, sensor 212, and/or any other suitable component that may be part of ITE component 102 and/or BTE component 104. For example, processor 214 may be configured to combine signals output from a plurality of microphones (e.g., microphone 202) based on the input audio signal to generate a directional microphone configuration in which sound coming from in front of the user is favored and sound coming from directions other than in front of the user is attenuated. Additionally or alternatively, processor 214 may control operation of sensor 212 in any suitable manner to detect a physiological attribute of a user.

By providing processor 214 as part of ITE component 102 in the exemplary configuration shown in FIG. 2A, it is possible to minimize the length of wiring connecting processor 214 to the various components (e.g., microphone 202, receiver 204, sensors 212, etc.) of ITE component 102. In so doing, it is possible to reduce disturbance from the wiring and/or efficiently utilize analog and/or digital communication interfaces provided as part of processor 214 to connect to the various components of hearing system 100.

Power source 216 is configured to provide operating power to BTE component 104 and/or ITE component 102. Power source 216 may include any suitable type of power source as may serve a particular implementation. For example, power source 216 may be implemented by a rechargeable lithium-ion battery in certain examples. In the exemplary configuration shown in FIG. 2A, power source 216 is provided in BTE component 104. With such a configuration, all of the operating power used to power the various components of ITE component 102 may be provided by way from BTE component 104 to ITE component 102 by way of cable 106. In such implementations, it is not necessary to have a power source such as a battery within ITE component 102, which frees up space within ITE component 102 for other components (e.g., sensors, a more powerful receiver, etc.) that may not have otherwise fit within ITE component 102. In addition, by providing power source 216 within BTE component 104 instead of ITE component 102, it is possible to provide a comparatively larger battery in hearing system 100 as there is more space behind the ear of the user than within the ear canal and/or concha.

In addition to power source 216, BTE component 104 may also include any suitable power management circuitry configured to manage charging power source 216 and/or any other suitable aspect associated with operation of power source 216.

In certain alternative implementations, an additional power source (not shown) may be included as part of ITE component 102. In such examples, the additional power source may operate together with power source 216 to provide operating power to ITE component 102 and/or BTE component 104. In addition, power source 216 may provide power by way of cable 106 to ITE component 102 to recharge the additional power source.

Wireless communication device 218 may operate according to any suitable wireless communication protocol to facilitate hearing system 100 communicating with an external device (e.g., a smartphone, a laptop computer, etc.). For example, wireless communication device 218 may be configured to operate according to a Bluetooth communication protocol, a Wi-Fi communication protocol, and/or any other suitable wireless communication protocol. Wireless communication device 218 may include any suitable components configured to facilitate communicating by way of a wireless communication protocol such as those described herein. For example, wireless communication device 218 may include an antenna configured to facilitate such wireless communication.

In the exemplary configuration shown in FIG. 2A, wireless communication device 218 is provided in BTE component 104 as opposed to ITE component 102. It is beneficial to provide wireless communication device 218 as part of BTE component 104 because the tissue that surrounds ITE component 102 while ITE component 102 is worn by a user typically absorbs wireless communication signals (e.g., 2.4 GHz based signals). Accordingly, it is possible to achieve better radiation patterns with the configuration shown in FIG. 2A than would be provided if wireless communication device 218 were part of ITE component 102 (e.g., if provided in the concha or the ear canal). In addition, by providing wireless communication device 218 as part of BTE component 104 as opposed to ITE component 102, it is possible to provide a relatively larger antenna, which may improve the capability of hearing system 100 to communicate wirelessly with an external device.

In certain alternative implementations, processor 214 may be included as part of BTE component 104, as shown in FIG.

2B, instead of ITE component 102. In such examples, a serial bus, such as those described herein, may be provided to facilitate BTE component 104 communicating with ITE component 102 by way of cable 106. Alternatively, processor 214 may be implemented by a plurality of processors distributed across ITE component 102 and BTE component 104 in any suitable manner to facilitate operation of hearing system 100.

Figure 3:
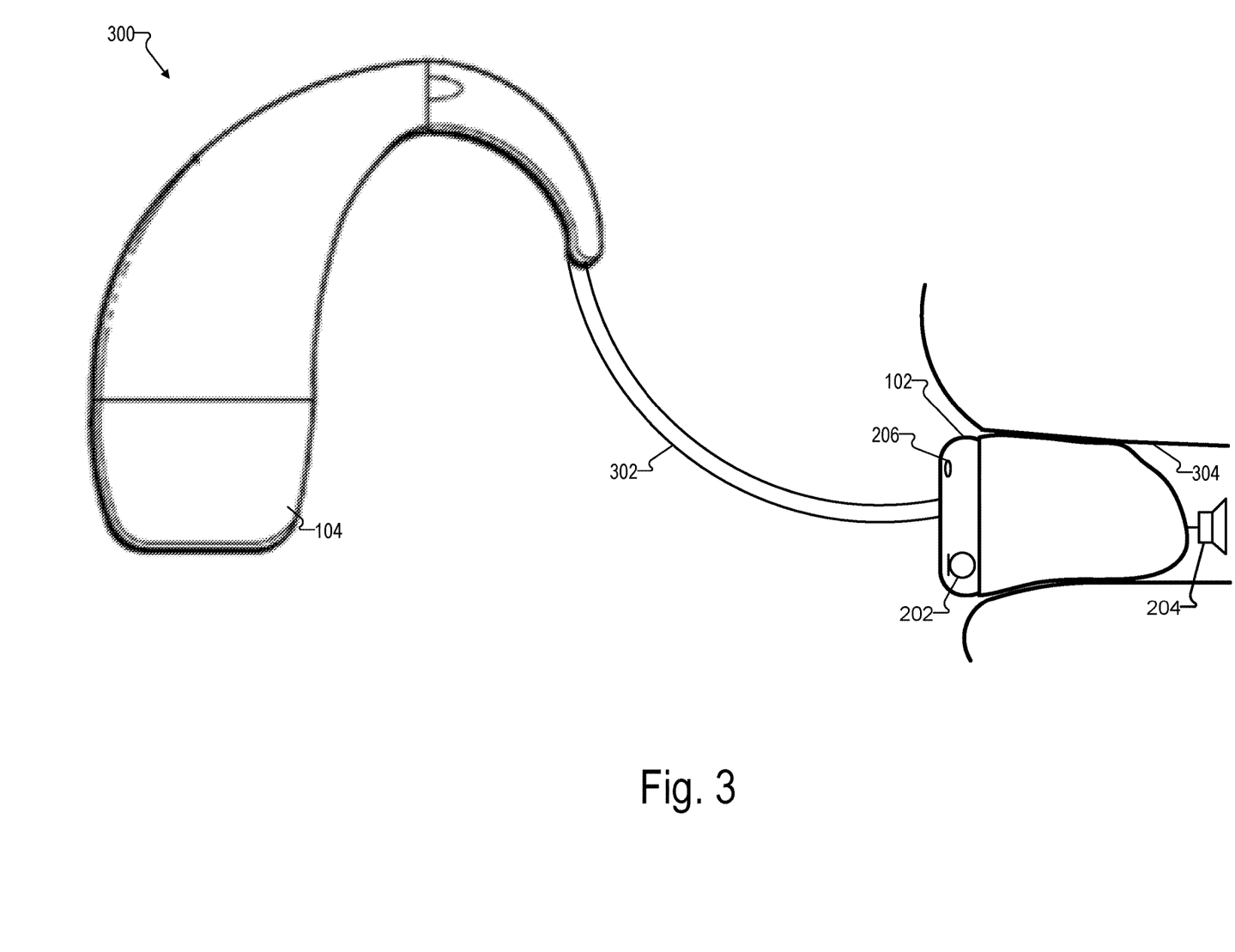
FIGS. 3 and 4 illustrate exemplary configurations of the hearing system shown in FIG. 1 according to principles described herein.

FIG. 3 shows an exemplary configuration 300 of hearing system 100 that may be provided according to certain implementations. As shown in FIG. 3, BTE component 104 is communicatively coupled to ITE component 102 by way of a cable 302. In FIG. 3, ITE component 102 is shown as including, without limitation, microphone 202, receiver 204, and vent opening 206. As shown in FIG. 3, ITE component 102 is provided at least partially within an ear canal 304 of a user. In the example shown in FIG. 3, vent opening 206 is provided on a surface of ITE component 102 that faces out of ear canal 304. Vent opening 206 is shown as having an oval shape in FIG. 3. However, vent opening 206 may have any suitable size and/or shape as may serve a particular implementation. For example, vent opening 206 may be slit shaped in certain alternative implementations. Microphone 202 is provided on a surface of ITE component 102 that faces out of ear canal 304. Receiver 204 is provided within ear canal 304. Receiver 204 is shown as extending away from ITE component 102 in FIG. 3 for illustrative purposes. It is understood that receiver 204 may be provided within a shell of ITE component 102 in certain implementations.

ITE component 102 is not limited to the particular components shown in FIG. 3. It is understood that ITE component 102 may include additional or alternative components, such as described herein. For example, ITE component 102 may also include one or more sensors (e.g., sensor 212), a processor (e.g., processor 214), and/or any other circuitry within a shell of ITE component 102.

Figure 4:
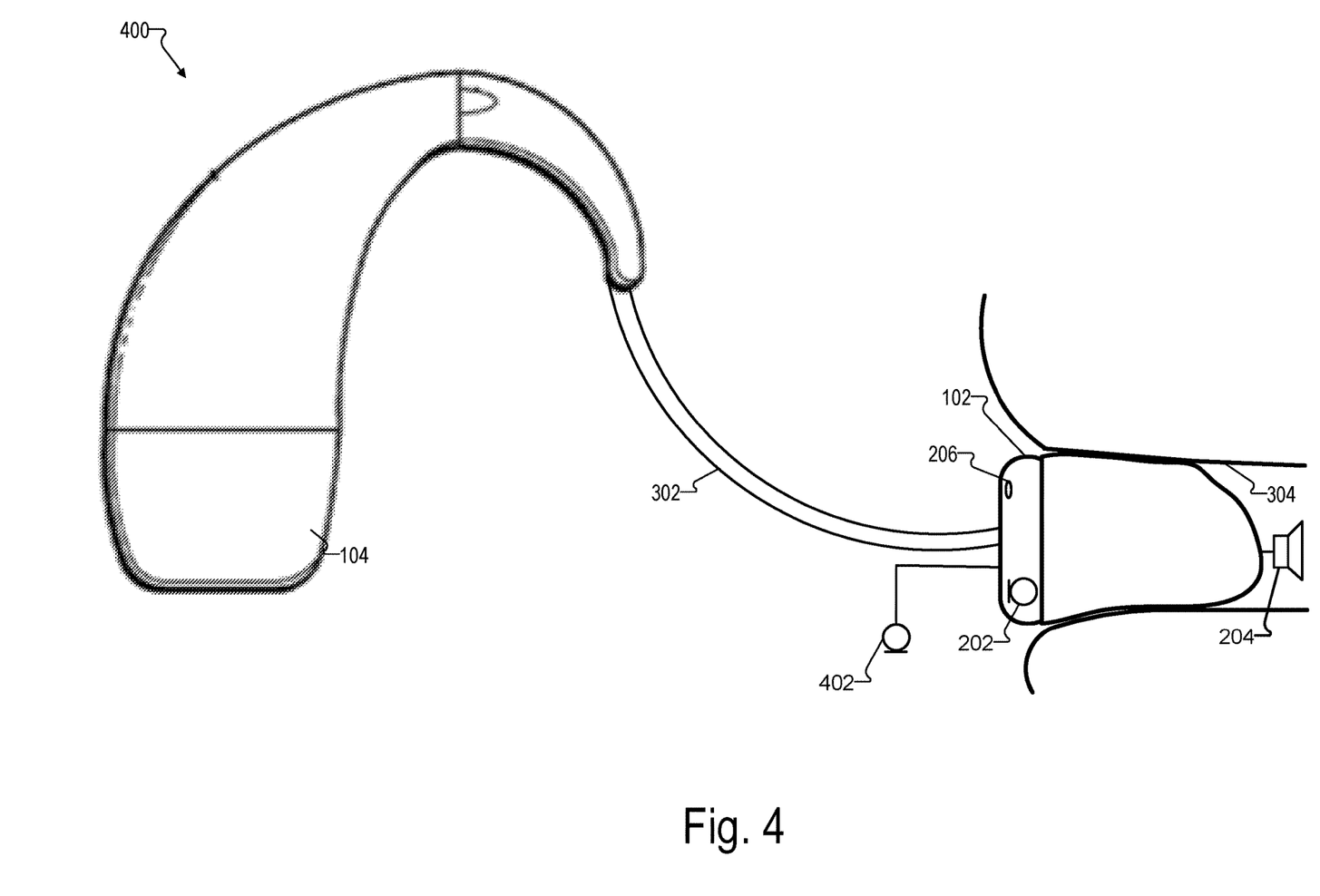

FIG. 4 shows an exemplary configuration 400 of hearing system 100 that may be provided according to certain implementations. Configuration 400 shown in FIG. 4 is similar to configuration 300 except that ITE component 102 is provided with an additional microphone 402. As shown in FIG. 4, additional microphone 402 extends outward from ITE component 102. In certain examples, microphone 402 may be a boom microphone that extends outward from ITE component 102 and towards a front of the user. With such a configuration, microphones 202 and 402 may form a directional microphone configuration in which sound coming from in front of the user is favored and sound coming from directions other than in front of the user is attenuated. As described herein, vent opening 206 may be positioned such that sound from receiver 204 that exits vent opening 206 impacts microphone 202 and additional microphone 402 from a direction that causes the sound from receiver 204 to be attenuated by the directional microphone configuration.

Figure 5:
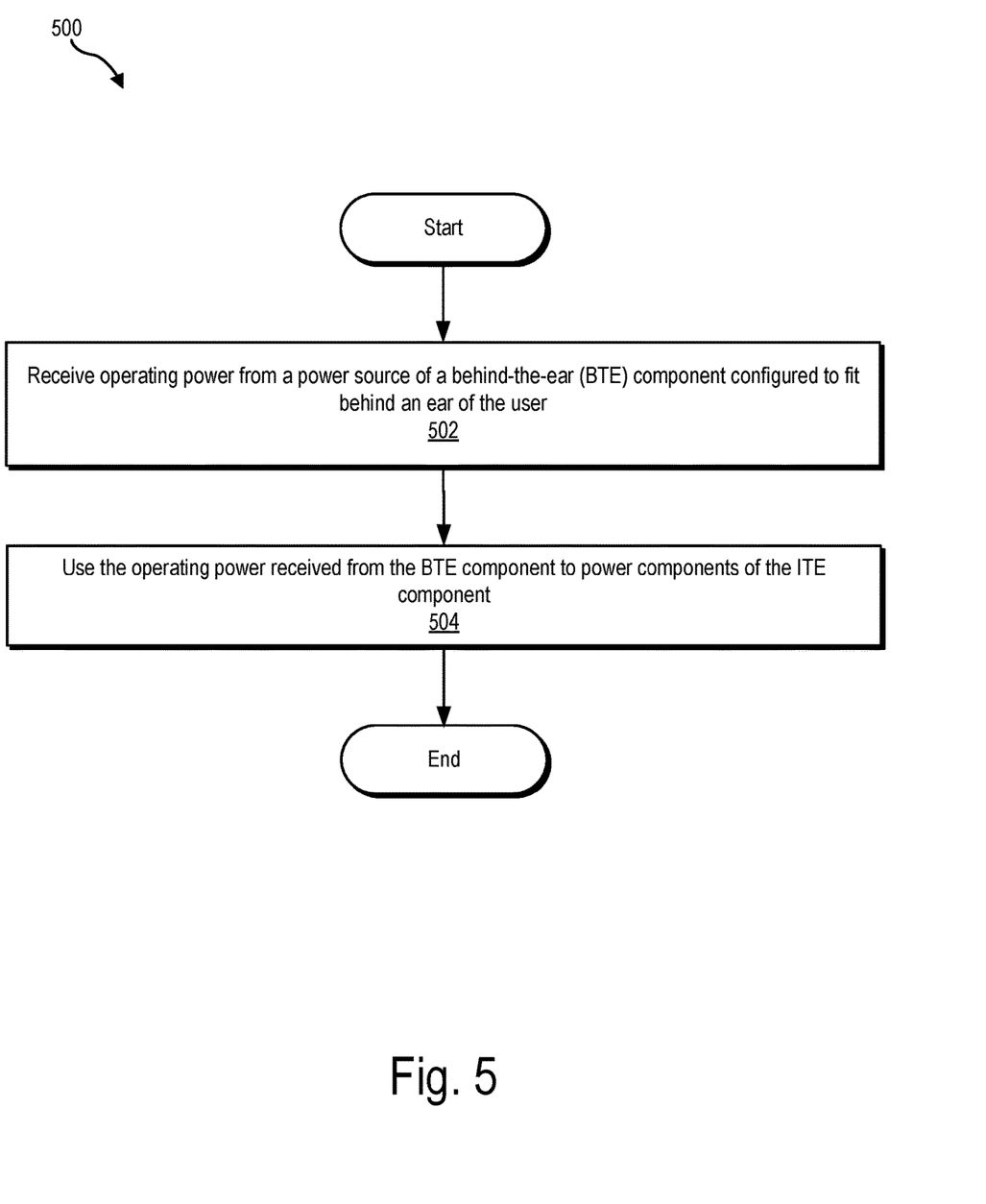
FIG. 5 illustrates an exemplary method for operating a hearing system according to principles described herein.

FIG. 5 illustrates an exemplary method for operating a hearing system according to principles described herein. While FIG. 5 illustrates exemplary operations according to one embodiment, other embodiments may omit, add to, reorder, and/or modify any of the operations shown in FIG. 5. One or more of the operations shown in FIG. 5 may be performed by processor 214 and/or any implementation thereof.

In operation 502, an ITE component (e.g., ITE component 102) receives operating power from a power source of a BTE component (e.g., BTE component 104) configured to fit behind an ear of the user. The operating power may be received by way of a cable that communicatively couples the BTE component with the ITE component. In certain examples, all of the operating power used by the ITE component may be provided from the power source of the BTE component. Operation 502 may be performed in any of the ways described herein.

In operation 504, the ITE component uses the operating power received from the BTE component to power components of the ITE component. As described herein, such components of the ITE component may include a microphone arranged so as to face outside of an ear canal of the user while the ITE component is worn by the user, a processor configured to process an input audio signal detected by the microphone, and a receiver configured to provide an audio signal detected by the microphone and processed by the processor. In certain examples, the processor may be further configured to process physiological signals and/or movement patterns detected by one or more sensors. Operation 504 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A hearing system configured to assist a user in hearing, the hearing system comprising:
   a behind-the-ear (BTE) component that is configured to fit behind an ear of the user and that includes a power source and power management circuitry configured to control the power source; and
   an in-the-ear (ITE) component configured to fit at least partially within an ear canal of the user while the hearing system is worn by the user, the ITE component including:
   a microphone arranged so as to face outside of the ear canal of the user while the ITE component is worn by the user;
   a vent opening configured to ventilate the ear canal of the user to an environment outside of the ear canal while the ITE component is worn by the user;
   a receiver configured to provide an audio signal to the user based on an input audio signal detected by the microphone; and
   at least one of
   active noise control circuitry configured to reduce at least one of environmental noise entering the ear canal through the vent opening and occlusion and
   an active vent configured to control the vent opening in the ITE component,
   wherein all operating power used to operate the ITE component is provided by the power source of the BTE component as controlled by the power management circuitry.

2. The hearing system of claim 1, wherein at least one of the BTE component and the ITE component further includes a processor configured to process the input audio signal detected by the microphone and direct the receiver to provide the audio signal to the user.

3. The hearing system of claim 2, wherein:
the ITE component includes an additional microphone that is arranged so as to face outside of the ear canal of the user while the ITE component is worn by the user; and
the processor is configured to combine signals output from the microphone and the additional microphone based on the input audio signal to generate a directional microphone configuration in which sound coming from in front of the user is favored and sound coming from directions other than in front of the user is attenuated.

4. The hearing system of claim 3, wherein the vent opening in the ITE component is positioned such that sound from the receiver that exits the vent opening impacts the microphone and the additional microphone from a direction that causes the sound from the receiver to be attenuated by the directional microphone configuration.

5. The hearing system of claim 1, wherein the BTE component includes a wireless communication device that is configured to communicate with an external device by way of a wireless communication protocol.

6. The hearing system of claim 1, wherein the ITE component further comprises at least one of:
a compass;
a gyroscope;
an accelerometer; and
a physiological sensor configured to detect a physiological attribute of the user while the hearing system is worn by the user.

7. The hearing system of claim 6, wherein the physiological sensor includes at least one of a photoplethysmogram sensor, a humidity sensor, a body temperature sensor, a glucose sensor, a blood pressure sensor, an electrocardiogram sensor, an electrooculography sensor, and an electroencephalogram sensor.

8. The hearing system of claim 1, wherein:
the ITE component includes the active noise control circuitry;
the ITE component further includes an additional microphone arranged so as to face inside the ear canal of the user while the ITE component is worn by the user; and
the active noise control circuitry is configured to use the additional microphone to reduce occlusion artefacts.

9. The hearing system of claim 1, wherein:
the ITE component includes the active noise control circuitry;
the ITE component further includes a dynamic speaker configured to be provided within a concha of the ear of the user while the ITE component is worn by the user; and
the active noise control circuitry is configured to use the dynamic speaker to reduce at least one of the environmental noise and occlusion artefacts.

10. The hearing system of claim 1, wherein the active vent is configured to be open while the user is speaking at a conversational level.

11. The hearing system of claim 1, further comprising a cable that communicatively connects the BTE component with the ITE component.

12. The hearing system of claim 11, wherein the cable includes at least one of a wire, an optical fiber, and a movable tube.

13. The hearing system of claim 12, wherein, when the cable includes the movable tube and at least one of the wire and the optical fiber, the at least one of the wire and the optical fiber is straightened when a distance between the BTE component and the ITE component increases and coils when the distance between the BTE component and the ITE component decreases.

14. The hearing system of claim 11, wherein the cable has a connector portion on one end such that the cable is removably attachable to one of the BTE component and the ITE component.

15. The hearing system of claim 11, wherein the cable has a connector portion on each end such that the cable is removably attachable to both the BTE component and the ITE component.

16. The hearing system of claim 11, wherein:
the cable uses a serial bus to facilitate communication between the BTE component and the ITE component; and
the serial bus is one of a proprietary bus, an inter-integrated circuit bus, a serial peripheral interface bus, an improved inter-integrated circuit bus, an optical bus, and an electrical system bus.

17. The hearing system of claim 1, wherein the microphone is a boom microphone.

18. A hearing system configured to assist a user in hearing, the hearing system comprising:
a behind-the-ear (BTE) component configured to fit behind an ear of the user, the BTE component including:
a power source;
power management circuitry configured to control the power source; and
a wireless communication device;
an in-the-ear (ITE) component configured to fit at least partially within an ear canal of the user while the hearing system is worn by the user, the ITE component including:
a microphone arranged so as to face outside the ear canal of the user while the ITE component is worn by the user;
a processor configured to process an input audio signal detected by the microphone; and
a receiver configured to provide an audio signal to the user based on the input audio signal detected by the microphone and processed by the processor; and
a cable that communicatively couples the BTE component with the ITE component,
wherein all operating power used to operate the ITE component is provided by the power source of the BTE component as controlled by the power management circuitry.

19. A method of operating a hearing system configured to assist a user in hearing, the method comprising:
receiving, by an in-the-ear (ITE) component configured to fit at least partially within an ear canal of the user, operating power from a power source of a behind-the-ear (BTE) component configured to fit behind an ear of the user, the power source controlled by power management circuitry included in the BTE component, the operating power received by way of a cable that communicatively couples the BTE component with the ITE component; and
using, by the ITE component, the operating power received from the BTE component to power components of the ITE component, the ITE component including:
a microphone arranged so as to face outside the ear canal of the user while the ITE component is worn by the user;

a processor configured to process an input audio signal detected by the microphone; and a receiver configured to provide an audio signal to the user based on the input audio signal detected by the microphone and processed by the processor, wherein all of the operating power used to operate the ITE component is provided by the power source of the BTE component as controlled by the power management circuitry.

* * * * *